United States Patent
Wachs et al.

[11] Patent Number: 6,147,263
[45] Date of Patent: Nov. 14, 2000

[54] FORMALDEHYDE PRODUCTION

[75] Inventors: Israel E. Wachs, Bridgewater, N.J.; Chuan-Bao Wang, Oakdale, Pa.

[73] Assignee: Lehigh University, Bethlehem, Pa.

[21] Appl. No.: 09/293,985

[22] Filed: Apr. 19, 1999

Related U.S. Application Data

[60] Provisional application No. 60/083,627, Apr. 30, 1998.

[51] Int. Cl.[7] .................................................. C07C 45/00
[52] U.S. Cl. ..................... 568/473; 568/472; 568/449; 502/350; 585/638; 585/640; 423/415.1; 423/512.1
[58] Field of Search ..................... 568/472, 473, 568/449; 502/350; 585/638, 640; 423/415.1, 512.1

[56] References Cited

U.S. PATENT DOCUMENTS

| | | | |
|---|---|---|---|
| 2,462,413 | 2/1949 | Meath | 260/603 |
| 2,519,788 | 8/1950 | Payne | 260/603 |
| 3,959,383 | 5/1976 | Northeimer | 260/603 |
| 3,965,195 | 6/1976 | Buschmann et al. | 260/603 HF |
| 3,987,017 | 10/1976 | Popoff et al. | 260/79.5 C |
| 4,072,717 | 2/1978 | Halbritter et al. | 260/603 C |
| 4,076,754 | 2/1978 | Kiser et al. | 260/603 C |
| 4,167,527 | 9/1979 | Nielsen | 260/603 C |
| 4,198,351 | 4/1980 | Branecky et al. | 260/603 C |
| 4,208,353 | 6/1980 | Webster et al. | 568/472 |
| 4,306,089 | 12/1981 | Webster et al. | 568/472 |
| 4,330,437 | 5/1982 | Krueger | 252/476 |
| 4,343,954 | 8/1982 | Hoene | 568/473 |
| 4,348,540 | 9/1982 | Ferris et al. | 568/472 |
| 4,454,354 | 6/1984 | Ferris et al. | 568/473 |

OTHER PUBLICATIONS

Deo, et al., "Reactivity of Supported Vanadium Pxode Catalysts: The Partial Oxidation of Methanol," J. Catal, 146, pp. 323–334, 1994.

*Primary Examiner*—Sreeni Padmanabhan
*Attorney, Agent, or Firm*—Banner & Witcoff, Ltd.

[57] ABSTRACT

A process for the catalytic conversion of methanol to formaldehyde wherein a gas stream containing methanol and oxygen is contacted with a silver catalyst in a first conversion zone containing a silver catalyst to produce an effluent containing formaldehyde, unreacted methanol, and oxidation byproducts; and contacting the first zone effluent with a copper catalyst in a second conversion zone for further conversion of the unreacted methanol. No molecular oxygen is added to the first stage effluent or to the second conversion zone.

15 Claims, 1 Drawing Sheet

FORMALDEHYDE PRODUCTION

This application claims the priority benefits from the U.S. provisional application Ser. No. 60/083,627 filed Apr. 30, 1998.

BACKGROUND OF THE INVENTION

1. Field of the Invention

This invention broadly relates to a process for the catalytic conversion of methanol to formaldehyde. In particular, the present invention relates to a process for preparing formaldehyde from methanol by contacting methanol and oxygen in contact with a first catalyst bed containing a silver catalyst, and passing the effluent from the first conversion into contact with a second catalyst bed containing an elemental copper catalyst.

2. Description of Related Art

There are primarily two commercially accepted processes for converting methanol to formaldehyde. The first utilizes a silver catalyst and operates in an oxygen lean atmosphere. The second utilizes a metal oxide catalyst and operates in a methanol lean atmosphere. The first process involves passing a mixture of methanol vapor and air over a fixed bed silver catalyst at approximately atmospheric pressure and absorbing the product gases in water. The mechanism by which methanol is converted to formaldehyde is believed to be a combination of two reactions separately involving the dehydrogenation and partial oxidation of methanol:

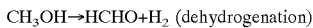
$CH_3OH \rightarrow HCHO + H_2$ (dehydrogenation)

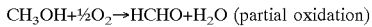
$CH_3OH + \frac{1}{2}O_2 \rightarrow HCHO + H_2O$ (partial oxidation)

Both single stage and multiple stage silver-catalyzed processes are known. Single stage operation is widely used but generally suffers from the disadvantage that rather high amounts of unconverted methanol are contained in the desired formaldehyde product emerging from the catalyst bed. For many applications, methanol is an undesirable contaminant in the formaldehyde product and must be separated from the recovered formaldehyde solution. Such recovery often entails a substantial investment in distillation facilities and energy to carry out such separations. Formaldehyde product specifications requiring a methanol content of no greater than 2% by weight are not uncommon.

One technique that has been suggested for eliminating the need for facilities to distill off methanol is sequential silver catalyst stages with interstage cooling. A basic two-stage catalytic process is disclosed in Meath U.S. Pat. No. 2,462,413.

Northeimer U.S. Pat. No. 3,959,383, purports to be an improvement of the Meath process involving the use of higher space velocities in the second stage converter and the employment of silver crystals of a specific particle size as the catalyst. These changes purportedly yield even lower amounts of methanol in the formaldehyde product.

Other two-stage processes have been described in the art. Payne, U.S. Pat. No. 2,519,788, describes a process for converting methanol to formaldehyde using an adiabatic first stage reactor for conducting methanol partial oxidation and dehydrogenation and containing a silver catalyst and an isothermal second stage reactor for conducting methanol oxidation and containing a metal oxide catalyst.

McClellan et al, in U.S. Pat. No. 3,987,107, disclose a two step, vapor phase process for converting methanol to formaldehyde. In the first step, methanol is contacted with a silver catalyst, while in the second step the remaining methanol, after inter-stage cooling and the introduction of auxiliary air, is contacted with a bismuth molybdate or bismuth phosphomolybdate-on-titania catalyst.

Efforts continue to be made to find new ways for further improving the conversion of methanol to formaldehyde without compromising selectivity. The present invention provides a two step catalytic process using known catalysts that allows such improvements to be obtained.

BRIEF DESCRIPTION OF THE DRAWINGS

The sole FIGURE is a schematic flow diagram illustrating the process of the present invention.

BRIEF DESCRIPTION OF THE INVENTION

Figure 1:
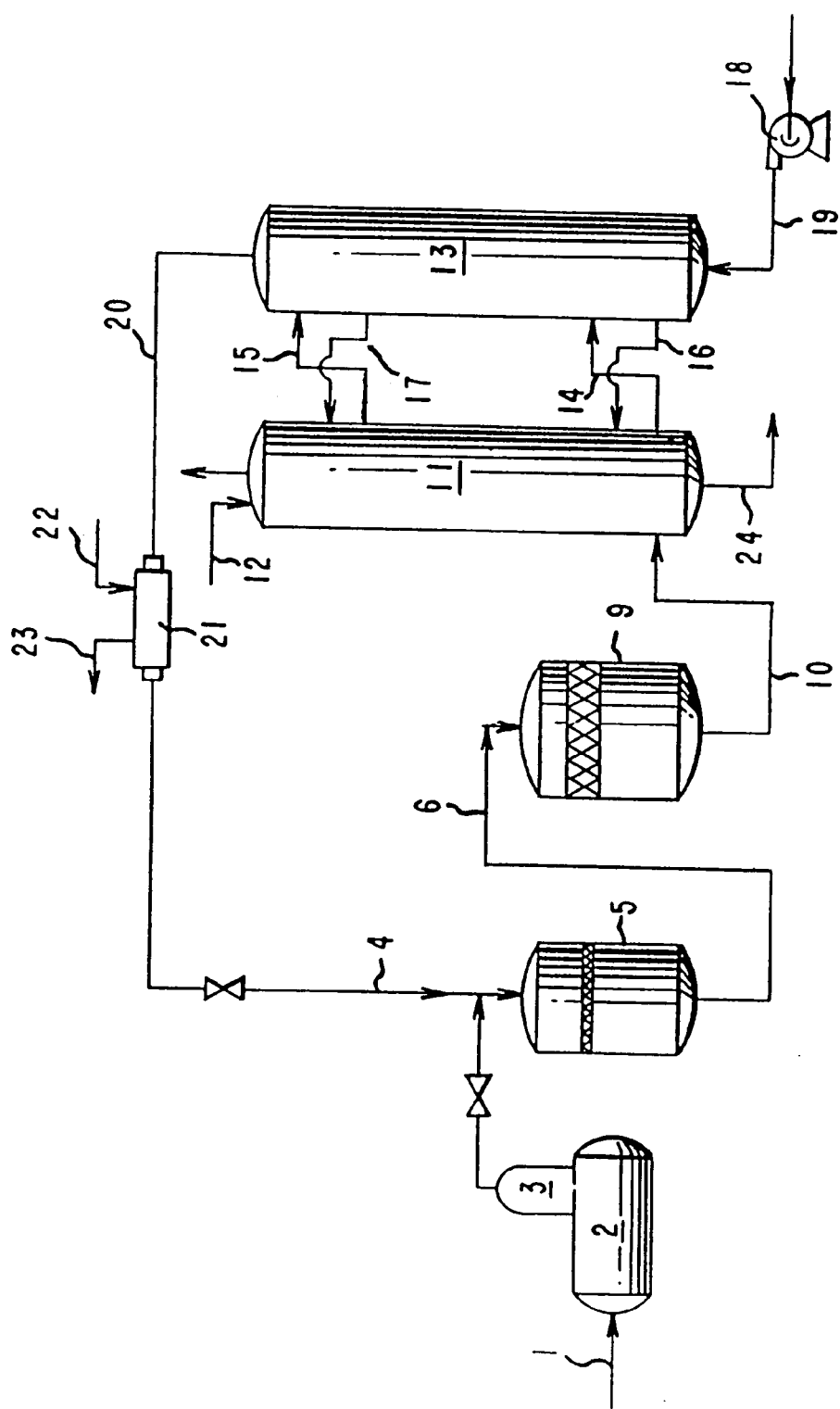

It is an object of the invention to provide a process for producing formaldehyde having a reduced level of methanol.

It is a further object of the invention to provide a catalytic process for producing formaldehyde by methanol oxidation in a first stage containing a first catalyst and molecular oxygen-free methanol conversion in a second stage containing a second catalyst.

In accordance with these another objects of the invention that will become apparent from the description herein, the process of the present invention comprises:

contacting methanol and molecular oxygen with a first catalyst containing silver for the production of formaldehyde in a first conversion zone to produce an effluent containing product formaldehyde, residual methanol, and oxidation byproducts substantially free of molecular oxygen, and contacting said effluent in the absence of free oxygen with a catalyst containing elemental copper for producing additional formaldehyde from methanol in said effluent.

The two stage process of the present invention produces higher yields of formaldehyde than were available with only the first stage catalyst while retaining high selectivity towards the manufacture of formaldehyde.

DETAILED DESCRIPTION OF THE INVENTION

The present invention has as its main objective to increase methanol conversion without sacrificing formaldehyde selectivity. In particular, applicants have discovered that by conducting a second stage of methanol conversion using an elemental copper catalyst in the substantial absence of molecular oxygen one can obtain an additional 30–40 percent conversion of the residual methanol that is generally discharged from the typical single stage operation of a conventional silver-containing catalyst. Importantly, sufficient selectivity for formaldehyde is retained such to obtain substantially the full effect of this increased conversion. In other words, the overall methanol conversion is increased from about 90 percent to about 93 to 94 percent, without incurring a comparable decrease in formaldehyde selectivity. Thus, the formaldehyde yield, based on the total methanol feed, is increased from about 78 to 80% to about 82 to 84%.

Methanol can be selectively oxidized to formaldehyde over a conventional silver catalyst using short contact times at a temperature within the range from about 500–700° C. and at a methanol/oxygen mole ratio generally in the range of 2–3. A formaldehyde selectivity of about 90 percent at a conversion of about 90 percent methanol is frequently chosen as target values representing an optimum balance of conversion and selectivity. In addition to water, the principal by-products are about 10 percent carbon dioxide and reaction byproducts including less than about 1 percent methyl formate (MF).

The formaldehyde catalyst used in the first conversion zone contains one or more forms of silver that is active for the dehydrogenation and partial oxidation of methanol and oxygen to form formaldehyde. Such silver-containing catalysts are well known in the art, e.g., U.S. Pat. Nos. 3,965,195; 4,072,717; 4,076,754; 4,198,351; and 4,343,954 the disclosures of which are herein incorporated by reference. The silver-based catalyst can be used in many forms including gauze, particles, fabrics, and crystals. A particularly preferred catalyst for formaldehyde conversion of methanol employs particulate silver having an average particle size of less than 1000 nm that is pretreated in a flowing gas containing helium and oxygen for an initially higher catalytic activity. (It will be understood that there may be some oxygen dissolved in the silver catalyst but that such silver oxide phases may not be stable at the conversion temperatures contemplated herein.)

Oxygen is added to or made to be present in the feed to the first conversion zone in an amount sufficient to provide a methanol conversion over the silver catalyst of 80 to 90% and preferably 84 to 90%. Normally, the methanol to oxygen mole ratio will provide methanol in sufficient excess to consume all oxygen in the first stage of the process. Generally, the methanol:oxygen range be in the range of 2 to 3 (molar). The source of oxygen, normally air, is added directly to the first conversion zone or as part of a process recycle stream.

Generally the pressure in the first conversion reactor will be from 5 to 15 psig (approximately 20 to 30 psia). In addition to the preferred silver catalyst, the first stage could also employ a mixed precious metal, silver-gold catalyst, for example as described in U.S. Pat. No. 4,167,527. A typical catalyst bed is 5 to 50 mm.

Both the characteristics of the catalyst itself and the operating conditions of the first stage are well understood by those skilled in the art. A detailed description can be found in *Kirk-Othmer Encyclopedia of Chemical Technology*, 4th Ed., Vol. 11 (John Wiley & Sons, Inc. (1994)), the relevant contents of which is herein incorporated by reference. At high methanol conversion rates, i.e., at least 80% of the methanol, the first stage reactor operates at a temperature in range of from 500° to 700° C. The gaseous effluent from the silver catalyst stage typically contains at least about 80% formaldehyde, about 10% unreacted methanol, and no free oxygen.

In accordance with the present invention, this effluent gas from the silver conversion zone is passed directly into contact with a catalyst containing, and preferably consisting essentially of elemental copper at conditions sufficient to convert at least a portion of the methanol in the first stage effluent to additional formaldehyde. Preferably, the process is conducted to convert at least 5% of the methanol in the first stage effluent into formaldehyde product. Even more preferably, 10–50% of the methanol from the first stage conversion is converted to formaldehyde with minimum affect on the formaldehyde product formed in the first conversion zone.

In a preferred form of the invention, no source of elemental oxygen (gas or liquid) is added to the feed stream entering the copper-catalyzed second stage. The oxygen-containing by-product species from the first conversion zone, particularly water ($H_2O$) and carbon dioxide ($CO_2$), provide whatever oxygen is needed for converting residual methanol to formaldehyde in the second conversion zone.

Generally, the second conversion zone is operated at a temperature in the range of 500° to 700° C. and at or just slightly above atmospheric pressure, preferably at a pressure of about 16–18 psia. The temperature may be maintained at a predetermined set temperature (isothermal) or allowed to progress without added or removed heat (adiabatic). Sub-atmospheric pressures should be generally avoided or used with caution to prevent the inadvertent introduction of oxygen into the process stream.

Copper catalysts useful for the invention that have hitherto been used for the catalytic conversion of methanol to formaldehyde are well known in the art. In such catalysts, the copper is present in the catalyst as elemental metal at the start of the reaction. A suitable copper catalyst can be prepared by reducing copper oxide in a helium gas stream containing about 5 volume percent hydrogen at a temperature of about 250°–400° C. A suitable copper catalyst can be prepared, for example, by reducing supported, unsupported, or particulate copper oxide, or a copper salt such as nitrate, bicarbonate, carbonate, acetate or oxalate. The copper catalyst can also be formed into gauze, fabric, honeycombs, or other structure that facilitates contact between the catalytic surfaces and the residual methanol from the first conversion zone.

The second catalyst conversion zone is designed to provide a throughput in the range of about 0.1–1 kg, preferably 0.25–0.75 kg, of residual methanol per kg of copper catalyst per hour. Under these conditions, it has been found that any decomposition or further oxidation of formaldehyde that might occur is minimal and is more than offset by the additional production of formaldehyde from the residual methanol. As a result, the overall yield of formaldehyde from the process increases.

The amount of copper used in the second conversion zone will depend on the efficiency of the conversion over the silver catalyst. In general, a weight ratio of copper catalyst to silver catalyst (Cu:Ag) will be within the range from about 6:1 to about 1:1 and preferably within the range of about 3.75:1 to about 4.25:1. A Cu:Ag catalyst weight ratio of about 4:1 is particularly preferred.

The process of the present invention can be performed with each conversion zone disposed in separate, sequential reactors (each containing a separate catalyst bed), in the same reactor vessel containing two beds disposed sequentially along the flow path of the reactants, or some other configuration that provides for the flow of effluent from the first conversion zone into the second conversion zone. Each zone can use catalyst in the form of either a fixed or moving bed. The choice of a particular reactor design is well within the skill of the existing level of skill in the art. In general, the use of sequential, fixed catalyst beds is preferred.

An embodiment of the present invention will be described with reference to FIG. 1. A stream of methanol 1 is fed to a methanol vaporizer 2 and superheater 3 where the methanol is vaporized and heated typically to a temperature in the range of from 160° to 180° C. Pure methanol or technical grade methanol may be used as a starting material for the process. The heated methanol stream can be mixed with recycle line 4, which typically contains 45 to 55 volume % of an inert gas, generally nitrogen from air, 12 to 14 volume % oxygen, 1.6 to 2.0 volume % of unreacted methanol, from 27 to 33 volume % water and from 4.0 to 4.8 volume % formaldehyde also at from 160° to 180° C. The combined stream is fed to a first conversion zone shown as first reactor 5 containing a silver catalyst. The dehydrogenation/partial oxidation of methanol to formaldehyde over this catalyst is exothermic. The temperature normally is controlled in part by regulating the air to methanol ratio and in part by the quenching effects of recycled, non-reactive gases (typically nitrogen and water).

The effluent gases from the first reactor 5 containing formaldehyde in a first gas product, may optionally be cooled to a temperature within the range from about 200° to about 240° C. (not shown). Such interstage cooling can be performed to minimize decomposition for formaldehyde product from the first conversion. In any event, the effluent from first reactor 5 is fed through line 6 into a second conversion zone shown as second reactor 9 containing a catalyst of elemental copper. Although the embodiment is not shown, a single reactor can be used with sequential reaction zones.

External cooling of second reactor 9 is not generally necessary. By only having what amounts to about 10–20 volume percent (preferably 10–15 vol %) unreacted methanol from the first reactor fed to the secondary reactor, the conversion of this remaining methanol is more or less self-regulating or sufficiently dilute to avoid concerns that the catalyst bed temperature might rise to a temperature where the copper catalyst becomes deactivated.

The product gas effluent from second reactor 9 is fed through line 10 to an absorber 11. Water is fed to absorber 11 through line 12 to absorb product formaldehyde from the gas. Generally, the water will be at temperature within the range from about 10° to 30° C. and is fed at a rate sufficient to provide a formaldehyde concentration within the range from about 52 to 59 wt % the water solution as product.

In the illustrated embodiment, a portion of the bottoms from absorber 11 is feed to the bottom of the stripper 13 via line 14. Additionally, a high side stream from absorber 11 also may be fed to the top half of the stripper 13 via line 15. Liquid returns from the stripper to the absorber are shown at line 16 and 17. Air is fed by compressor 18 through line 19 to stripper 13. Alternately, air can be pulled through the stripper by installing the blower in line 20. Air saturated with water vapor, methanol and formaldehyde is recycled from stripper 13 via line 20, first through superheater 21 and then on to primary reactor 5 and secondary reactor 9. Superheater 21 heats the gases passing therethrough as needed to maintain appropriate temperatures in the primary and secondary reactors. Normally, the gas exiting the superheater will be at a temperature in the range of from 160° to 180° C. Product formaldehyde is removed in line 24 as a stream which contains for example 52 to 59 wt. % formaldehyde.

EXAMPLES

To facilitate a more complete understanding of the invention, the following Examples are provided below. The scope of the invention, however, is not limited to specific embodiments disclosed in these Examples, which are for purposes of illustration only.

Example 1

Catalyst Preparation

Silver catalyst for the first stage conversion reaction was obtained from a commercial source. The silver catalyst was at a particle size within the range of 30–60 mesh (250–550 μm). The silver catalyst was pretreated for 30 min at 500° C. with a flowing gas stream containing 5% oxygen in helium before beginning the methanol oxidation.

Particulate copper catalyst was prepared by reducing CuO in a flowing gas stream of 5% hydrogen in helium at 250° C. for 0.5 hr and then at 400° C. for an additional 2.5 hr.

Examples 2–4

Formaldehyde Production

Methanol conversion to formaldehyde was performed in a fixed bed reactor using a double bed configuration in a single reactor vessel. See, *J. Catal.*, 146, pp. 323–334 (1994). The first bed in each example contained 100 mg of pretreated silver catalyst. The conversion through the first bed reflects the prior art process. (Ex. 2)

The second bed contained particulate copper catalyst in an amount of either 100 mg (ex. 3) or 400 mg (ex. 4). A gas mixture of methanol/oxygen/helium (6.2/2.4/91.4 by volume) was used as the feed at a total flow rate of 100 ml/min. A gas chromatograph equipped with appropriate detectors was used to analyze the reactants and products. See, *J. Catal.*, 146 pp. 323–334 (1994). The conversions over each catalyst bed are reported in Table 1.

TABLE 1

| | Conversion (%) | | Selectivity (%) | | | | | |
|---|---|---|---|---|---|---|---|---|
| | | | HCH | | DM | | | |
| Example | MeOH | $O_2$ | O | MF | DME | M | CO | $CO_2$ |
| 2 Ag | 90.0 | 100 | 88.9 | 0.5 | 0.0 | 0.0 | 0.0 | 10.6 |
| 3 Ag/Cu | 93.4 | 100 | 88.8 | 0.5 | 0.0 | 0.0 | 0.0 | 10.7 |
| 4 Ag/Cu | 94.1 | 100 | 88.1 | 0.5 | 0.0 | 0.0 | 0.0 | 11.4 |

MF = methyl formate
DME = dimethyl ether
DMM = dimethoxy methane (methylal)

The conversion data of Table 1 show that additional conversion of methanol can be obtained by the use of a copper catalyst in a second conversion stage of methanol conversion effluent over a silver catalyst. Notably, the copper catalyst does not reduce the formaldehyde yield or materially affect its selectivity.

Example 5

Several formaldehyde conversion tests were conducted with various dehydrogenation catalysts in a second conversion zone following a first conversion zone containing the silver catalyst of example 1. In each case, the formaldehyde yield was adversely affected.

TABLE 2

| Catalyst | Effect on Formaldehyde Yield |
|---|---|
| Zinc chromate | formaldehyde decomposed to CO and $CO_2$ |
| K/Al-iron oxide | no further conversion |
| $Na_2CO_3$ | MeOH conversion decreased, formaldehyde selectivity decreased from 88.9% to 83.2%, $CO_2$ level increased from 10.6% to 14.6%, CO increased to 2.2% |

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

What is claimed is:

1. A process for producing formaldehyde from methanol by the steps comprising:

contacting a feed stream containing methanol and oxygen in a first conversion zone with a catalyst containing silver to form an effluent gas containing formaldehyde, unreacted methanol and oxidation products, and contacting said effluent in the absence of molecular oxygen in a second conversion zone with a catalyst consisting essentially of elemental copper to produce additional formaldehyde from said unreacted methanol.

2. A process according to claim 1 wherein conditions in said first conversion zone include a temperature within the range from about 500–700° C. and at a methanol/oxygen mole ratio within the range of about 2–3.

3. A process according to claim 1 wherein said first conversion zone contains particulate silver.

4. A process according to claim 1 further comprising the step of:

cooling said effluent between said first conversion zone and said second conversion zone.

5. A process according to claim 1 wherein effluent from said fist conversion zone is passed directly into said second conversion zone.

6. A process according to claim 1 wherein second conversion zone is operated at a temperature in the range of 500° to 700° C. and a pressure within the range of about 16–18 psia.

7. A process according to claim 1 wherein the copper catalyst in said second conversion zone has been reduced by contact with a flowing gas containing hydrogen.

8. A process according to claim 7 wherein said copper catalyst has been reduced by contact with hydrogen at a temperature within the range from about 250°–400° C.

9. A process according to claim 1 wherein the weight ratio of copper catalyst in said second conversion zone to silver catalyst in said first conversion zone is within the range from about 6:1 to about 1:1.

10. A process according to claim 1 wherein the weight ratio of copper catalyst in said second conversion zone to silver catalyst in said first conversion zone is within the range of about 3.75:1 to about 4.25:1.

11. A process according to claim 1 wherein the weight ratio of copper catalyst in said second conversion zone to silver catalyst in said first conversion zone is at a weight ratio of about 4:1.

12. A process according to claim 1 wherein said first conversion zone and said second conversion zone are within a single reactor vessel.

13. A process according to claim 1 wherein said first conversion zone and said nd conversion zone are in separate reactor vessels.

14. A process according to claim 1 wherein oxygen is provided to said first conversion zone to provide a methanol conversion over the silver catalyst of 80 to 90%.

15. A process according to claim 14 wherein at least 5 mol % of methanol in said effluent is converted to formaldehyde in said second conversion zone.

* * * * *